United States Patent
Bono et al.

(10) Patent No.: US 11,298,168 B2
(45) Date of Patent: Apr. 12, 2022

(54) ORTHOPEDIC SURGICAL METHOD, SYSTEM AND STRUCTURE FOR SECURING A BONE SCREW TO A BONE

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US)

(73) Assignee: Globus Medical, Inc., Audubon, PA (US)

( * ) Notice: Subject to any disclaimer, the term of this patent is extended or adjusted under 35 U.S.C. 154(b) by 154 days.

(21) Appl. No.: 16/743,620

(22) Filed: Jan. 15, 2020

(65) Prior Publication Data
US 2020/0222099 A1    Jul. 16, 2020

Related U.S. Application Data

(60) Provisional application No. 62/792,559, filed on Jan. 15, 2019.

(51) Int. Cl.
*A61B 17/70* (2006.01)
*A61B 17/86* (2006.01)

(52) U.S. Cl.
CPC ...... *A61B 17/8625* (2013.01); *A61B 17/7032* (2013.01); *A61B 17/7035* (2013.01)

(58) Field of Classification Search
CPC ............ A61B 17/8625; A61B 17/7032; A61B 17/7035; A61B 17/863; A61B 17/7055; A61B 17/846; A61B 17/866; A61B 17/8645; A61B 17/864; A61F 2/30988; A61F 2002/30782; A61F 2002/30769; A61F 2002/3092; A61F 2002/30995; A61F 2002/30622; F16B 25/0021; F16B 25/0047; F16B 25/078; F16B 33/006; F16B 35/041; F16B 37/005
USPC ........................................................ 606/312
See application file for complete search history.

(56) References Cited

U.S. PATENT DOCUMENTS

| | | | |
|---|---|---|---|
| 7,179,036 B2 * | 2/2007 | Griffin | F16B 25/0021 411/301 |
| 7,335,201 B2 | 2/2008 | Doubler et al. | |
| 8,075,603 B2 | 12/2011 | Hammill, Sr. et al. | |
| 2013/0172902 A1 * | 7/2013 | Lightcap | A61B 5/4836 606/130 |
| 2016/0235481 A1 * | 8/2016 | Dorman | A61B 17/1703 |
| 2019/0216553 A1 | 7/2019 | Bono | |
| 2019/0216560 A1 | 7/2019 | Bono et al. | |

* cited by examiner

*Primary Examiner* — Pedro Philogene (57) ABSTRACT

The present invention provides a method of forming pilot apertures for surgical screws. The method provides at least three points of contact to the screw shank to provide reliable positioning and retention of the bone screw. The method also provides slots or areas for insertion and retention of bone growth promoting materials which further secure the bone screw over time. The method is useful for patients of all ages, and may be particularly useful for patients that have osteoporosis or patients that are very active by providing additional securement of the bone screw to the underlying bone.

15 Claims, 9 Drawing Sheets

ORTHOPEDIC SURGICAL METHOD, SYSTEM AND STRUCTURE FOR SECURING A BONE SCREW TO A BONE

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/792,559, entitled "ORTHOPEDIC SURGICAL METHOD, SYSTEM AND STRUCTURE FOR SECURING A BONE SCREW TO A BONE", filed Jan. 15, 2019. The contents of the above referenced application are incorporated herein by reference in its entirety.

FIELD OF THE INVENTION

A surgical method of implanting an orthopedic screw and surgical structure.

BACKGROUND OF THE INVENTION

The present invention relates to a method, system and structure of installing a surgical orthopedic screw to a patient's bone. Surgical screws, such as pedicle screws, are well known in the art, as are their methods of installation. One current method is to force form a pilot hole with an instrument such as a Jamshidi needle; Jamshidi needles are well known in the art. The screw is then installed by having its threaded shank threadably inserted into the formed hole by rotation of the screw shank. The pilot hole guides the screw movement on a desired and predetermined path of movement. The pilot hole forming needle does not form machining residue. Such hole formation often requires a large amount of force to effect its penetration. Such force can, however, be highly variable between patients and along the path of penetration, and the bone structure changes from the bone exterior to interior. In addition, the screw shank diameter is typically much larger that the pilot hole diameter, often times requiring high torque being applied to effect screw insertion.

A machining tool (or robotic effector) can form a machined pilot hole by removing bone material. Such tools can include a drill bit that principally cuts or machines with its tip end. Machining can also include cutting with the side of a cutting or grinding tool. Such tools are rotated about their longitudinal axis or axis of rotation. Such machining creates machining residue that can interfere with screw insertion. Generally, the diameter of the machined pilot hole is smaller than the minor or root diameter of the screw so there is good strength of screw attachment and threads are formed as the screw is inserted. In some case, a thread forming tap is inserted prior to the screw to make screw insertion easier and reduce the compressive load to the bone caused by forcing the thread formation. The tap generally cuts the threads by removing small amounts of material to form the threads.

It is often desirable to add material at orthopedic surgical sites to induce bone growth around implants. Such materials include demineralized bone, morselized bone, and bone cement to increase strength of the screw/bone assembly. Current screw attachment methods preclude addition of such materials or cause the material to be wiped away as the screw is inserted. In the formation of pilot holes for screw insertion, there is no space between the screw shank and surface defining the pilot hole except at the tapered tip end of the screw. Thus, what is needed in the art is a screw aperture that provides three-point contact to the screw shank to provide positive positioning of the screw. The screw aperture should also provide slots for addition of bone growth material to strengthen the bond between the bone screw and the underlying bone.

DESCRIPTION OF THE PRIOR ART

The use and design of pedicle screws are disclosed in U.S. Pat. Nos. 8,075,603 and 7,335,201. To the extent of a general description of the details and use of a pedicle screw, the disclosures of these patents are incorporated herein by reference.

SUMMARY OF THE INVENTION

Briefly, the present invention provides a method of forming pilot apertures for surgical screws. The method provides at least three points of contact to the screw shank to provide reliable positioning and retention of the bone screw. The method also provides slots or areas for insertion and retention of bone growth promoting materials which further secure the bone screw over time. The method is useful for patients of all ages, and may be particularly useful for patients that have osteoporosis or patients that are very active by providing additional securement of the bone screw to the underlying bone.

Thus, it is an objective of the present invention to provide a method for installing orthopedic bone screws into bone.

It is another objective of the present invention to provide a method for installing orthopedic bone screws that is an improvement on current processes and final surgical site structures.

It is a further objective of the present invention to provide a method for installing orthopedic bone screws that provides channels or slots for the use of bone growth material with a screw.

It is yet another objective of the present invention to provide an orthopedic surgical site for screw installation that can be used to induce new bone growth.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
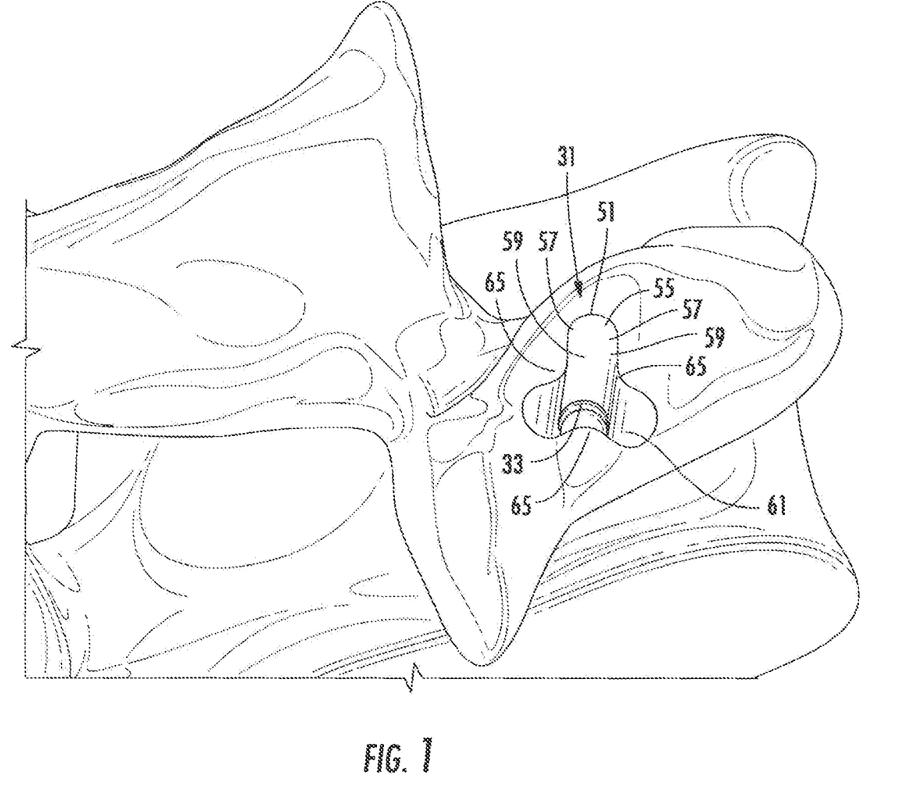
FIG. 1 is an orthopedic skeletal surgical site showing a pilot hole for bone screw insertion.
Figure 2:
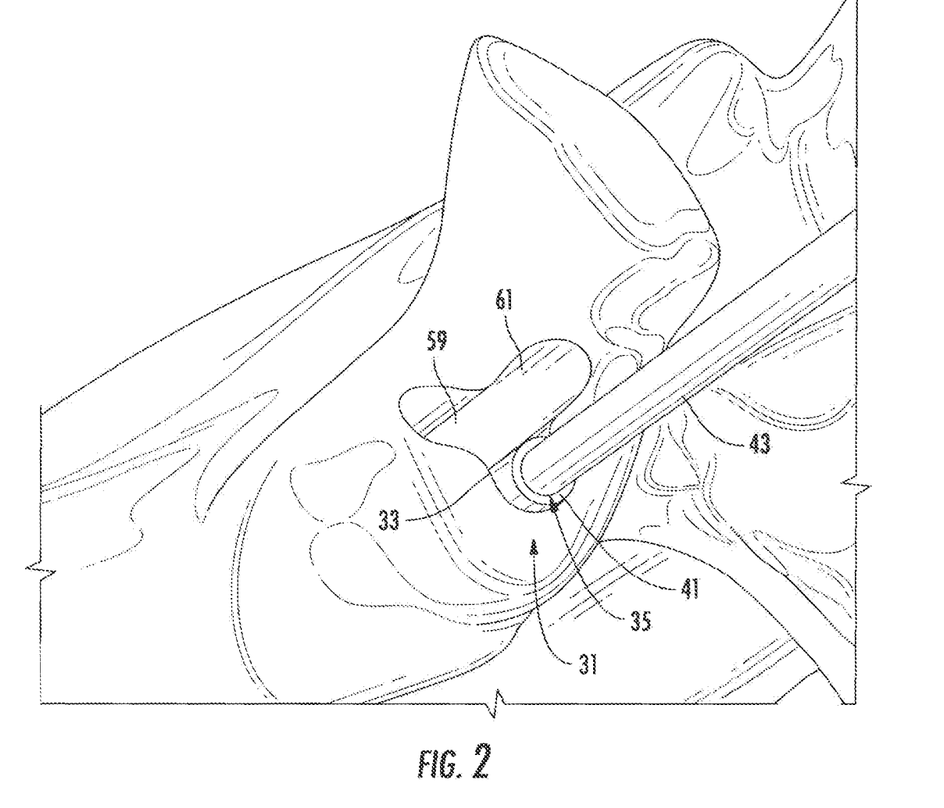
FIG. 2 is a perspective view of the surgical site with a machining effector forming the pilot hole.
Figure 3:
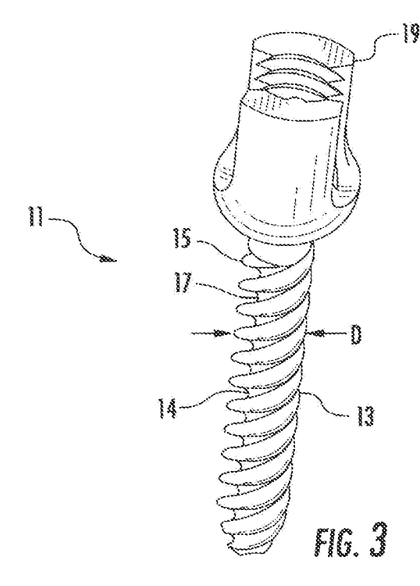
FIG. 3 is an isometric view of an example of a pedicle screw.
Figure 4:
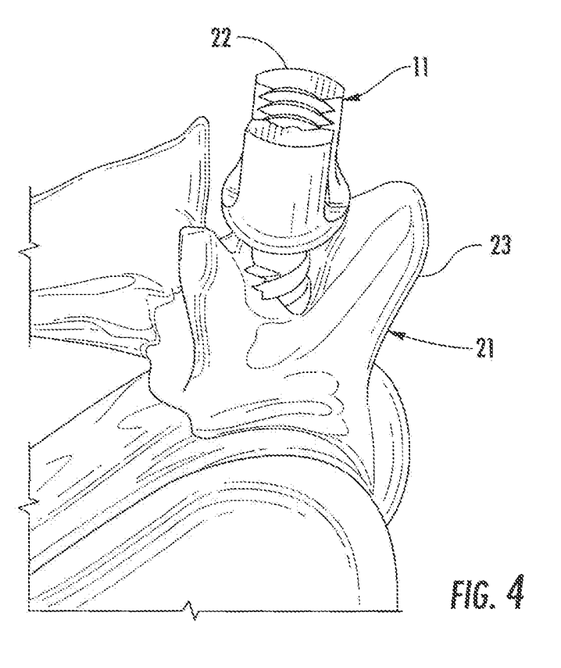
FIG. 4 is an isometric view of a skeletal bone with a pedicle screw in the pilot hole of FIG. 1.
Figure 7:
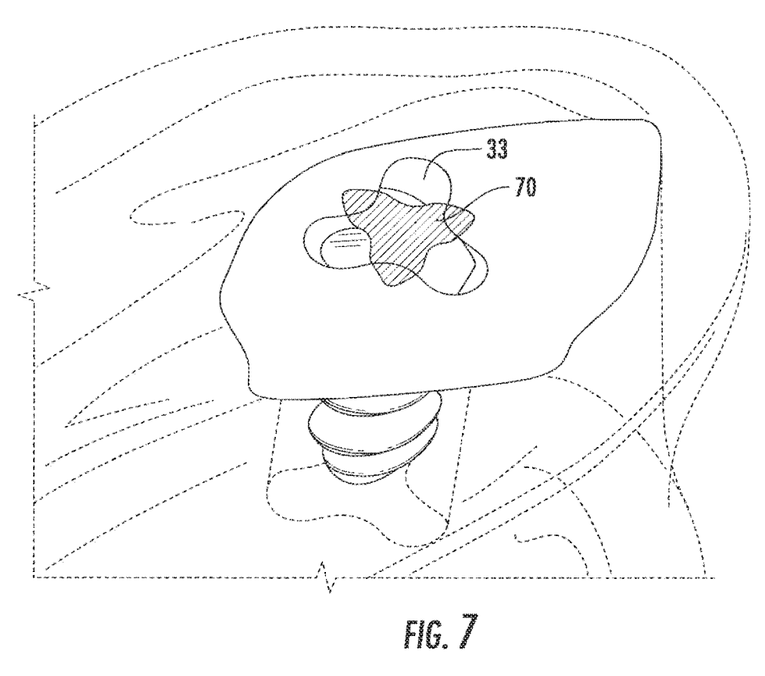
FIG. 7 is a section view taken along lines 7-7 of FIG. 6, illustrating the cooperation of the shank with the bone.
Figure 8:
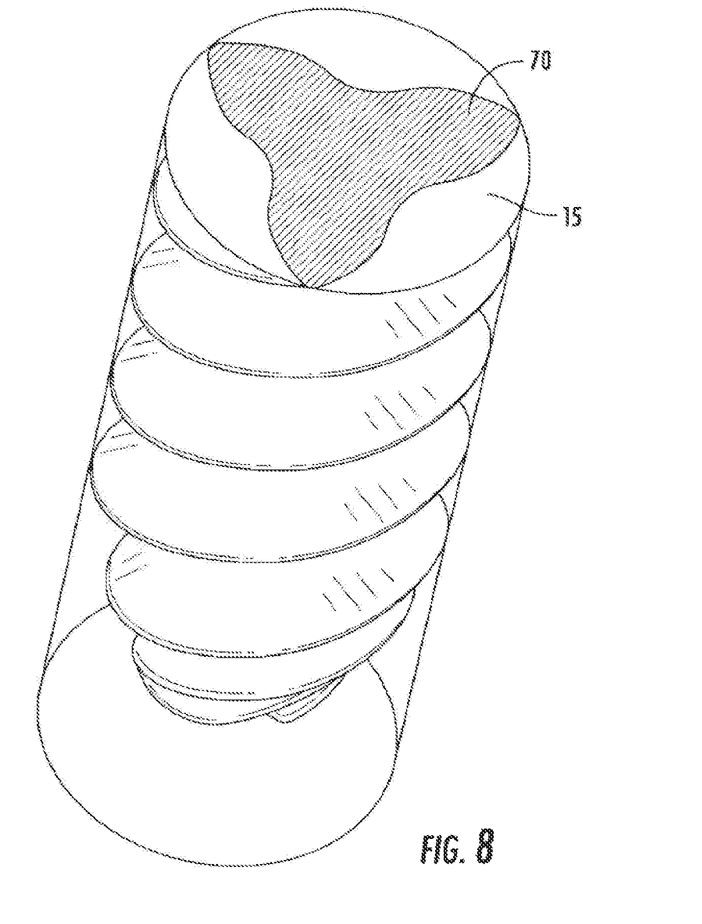
FIG. 8 is an isometric section view taken along lines 8-8 of FIG. 6, illustrating the tri-lobe shank.
Figure 9:
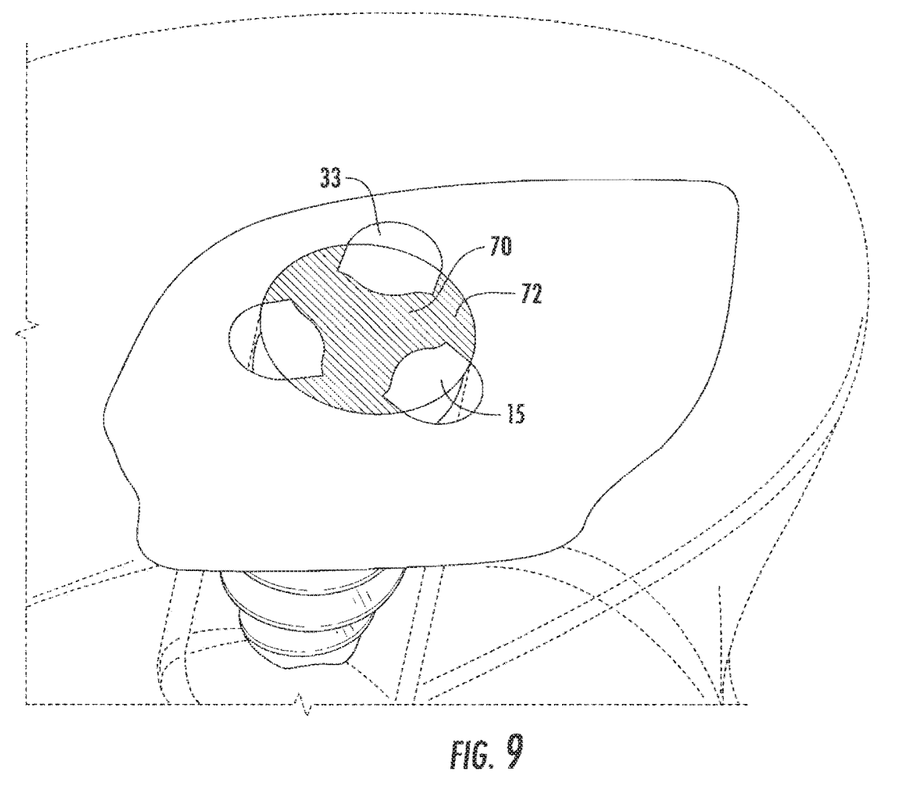
FIG. 9 is a partial section view taken along lines 9-9 of FIG. 6, illustrating the cooperation of the shank and thread with respect to the bone.

Referring to FIGS. 1-10, a method, system and structure for securing a bone screw to a bone in a surgical procedure is illustrated and described. FIG. 3 illustrates a surgical screw in the form of a pedicle screw 11 useful with the present invention. As used herein, the screw 11, when it has a cylindrical threaded shank section, has a major thread diameter D that is the diameter of an imaginary coaxial cylinder that just touches the crest of an external thread in the cylindrical portion of the screw 11. It is to be understood that the shank 13 can be a tapered shank. Such screws are self-tapping screws and preferably of a gimlet style or cone point threaded shank 13. It is to be understood, however, that any suitable type of screw shank can be utilized for the screw 11. While the present invention will be described in terms of the use of a pedicle screw, it is to be understood that other types of surgical screws can be used. The screw shank 13, for a shank that has a generally cylindrical shank section, has a minor or root diameter (as that term is used in the art), which is the diameter of an imaginary cylinder that just touches the root 17 of the external thread 15 in its cylindrical portion of the screw 11. The root 17 is the bottom of the groove between two flanking surfaces of the thread 15. The thread 15 can be a single thread or a dual thread, as is known in the art. The threaded portion can have different pitch sections. A pedicle screw 11 includes a tulip 19, as is known in the art, for securement of a rod (not shown) to the screw 11. The tulip 19 is pivotally mounted on the shank 13, as is well known in the art, for poly-axial pedicle screws. It is to be understood that the pedicle screw 11 could be a mono-axial screw or the tulip could be fixed to the screw without departing from the scope of the invention. The screw shank 13 will be associated with a driver element (not shown), such as a spline, hex or other shaped socket, which will provide a means for a driver to couple with the screw 11 to drive it into an orthopedic feature, such as a vertebral bone 21. In the illustrated structure of FIG. 4, the bone 21 is a vertebra having a pedicle portion 23. Preferably, the driver element is integral with the shank 13. Such pedicle screws are well known in the art. The tulip 19 can be internally threaded to receive a set screw (not shown) for securing a rod in the saddle portion 22 of the tulip 19. FIGS. 6-9 illustrate an alternative embodiment of the screw 11. This embodiment of the screw 11 includes a tri-lobe shank 70 and standard threads for cooperation with a bone. In this embodiment, the shank 13 would provide compression to the innermost points of the pilot hole 33. This construction may be particularly useful for patients having osteoporosis by limiting the load to the surrounding bone while still compressing the bone sufficiently to gain a good purchase, and thus good pull out strength to the screw 11. FIG. 7 illustrates the preferred cross sectional shape of the shank 13. FIG. 8 illustrates the relationship of the shank to the outer diameter of the threads 15. FIG. 9 illustrates the areas of compression 72 provided by the cooperation of the shank 70 and threads 15 to the shaped pilot hole 33.

Figure 5:
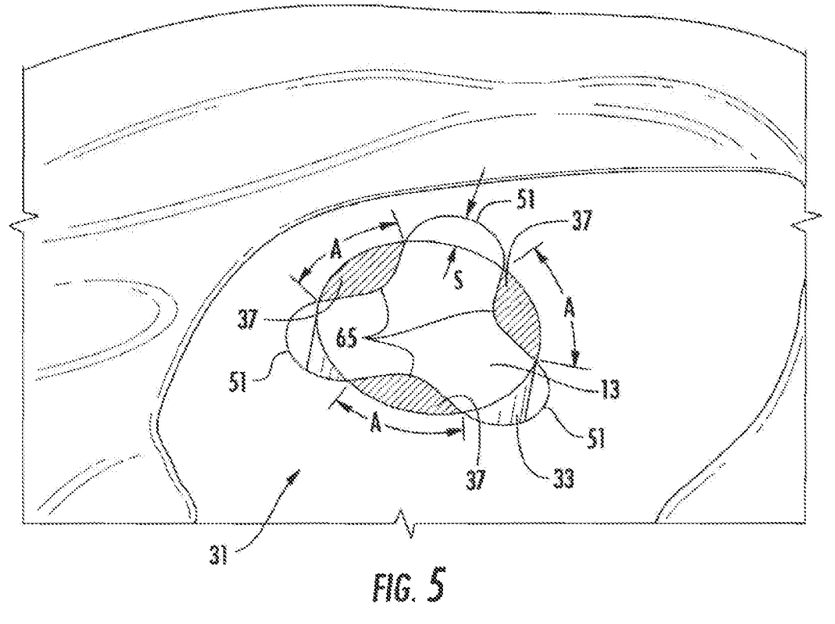
FIG. 5 is an isometric schematic view of the area of screw engagement with a skeletal bone illustrating screw purchase with the bone.
Figure 6:
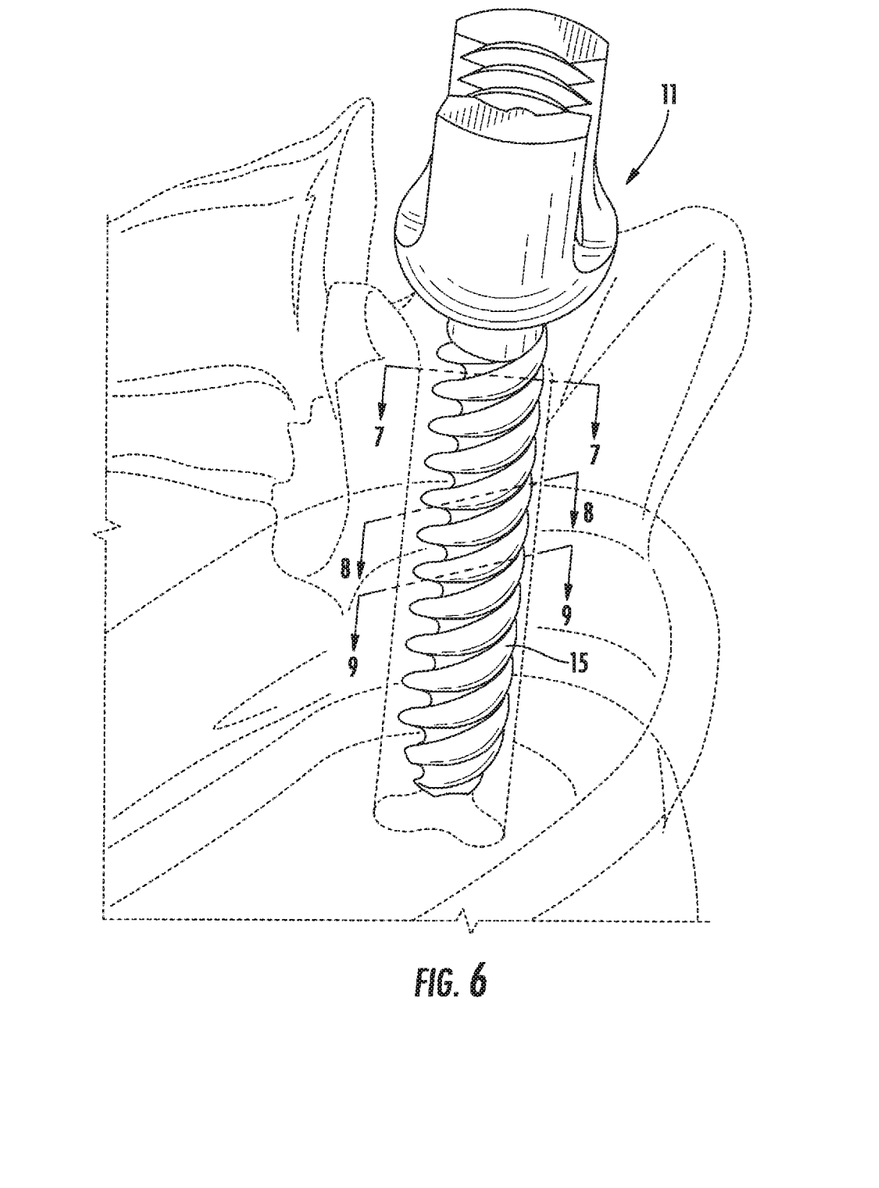
FIG. 6 is an isometric view illustrating an alternative embodiment of a pedicle screw having a tri-lobe shank at its minor diameter.

FIGS. 1, 2 and 5 show a surgical site 31 with a pilot hole 33 useful for receiving the shank 13 of a screw 11 therein. FIG. 2 shows the pilot hole 33 with a hole forming effector 35 therein; while FIG. 5 shows the pilot hole 33 schematically with a shank 13 installed in the pilot hole 33 and illustrates purchase areas 37. As used in the art, a purchase area 37 is that area of engagement between a screw thread and bone when the screw shank 13 is in engagement with the bone in the cylindrical portion of the screw shank 13. As used herein, a purchase is that area of engagement between the screw shank 13 and bone 21 in the area of the shank adjacent the tulip 19 or end portion of the screw 11 immediately adjacent the exposed outer surface of the bone 21 in which the screw 11 is installed. The effector 35 is shown as having a machining element 41 attached to a shaft 43, which in turn is coupled to a drive device (not shown) such as an electric motor or other powered rotary device. In a preferred embodiment, the shaft 43 would be coupled to a drive device that is part of a surgical robot (not shown) that will control operation of the machining element 41. A preferred machining element 41 would be able to machine bone with its distal or free end and on its side. Movement of the machining element 41 can be controlled in all three axes by the robot (not shown). Such robots are well known in the art. Such a robot is disclosed in our co-pending patent application Ser. Nos. 62/616,673; 62/681,462; 62/423,651; 62/616,700; 62/681,462 and 15/816,861 to Peter L. Bono. Alternatively, the machining element 41 and the remainder of the effector 35 can be coupled to a manually controlled powered driver, such as an electric motor that is part of a surgical tool as is known in the art. A manually operated powered driver with effector 35 can be used in combination with a guide jig (not shown) suitably held in place to effect pilot hole formation.

Figure 10:
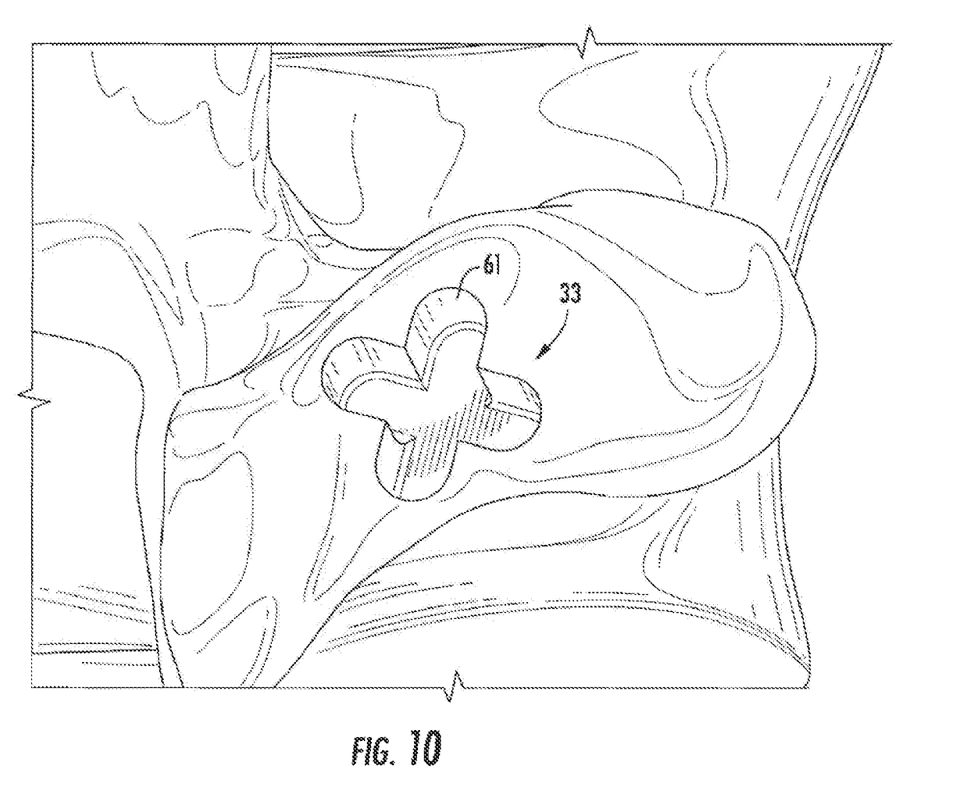
FIG. 10 is an alternative construction of the pilot hole having four lobes.

The pilot hole 33 has a plurality of lobes 51, as best seen in FIG. 5. At least three lobes 51 are needed, while four lobes 51 are shown in FIG. 10. The lobes 51 project generally radially outwardly from a center of the pilot hole 33, and preferably are spaced circumferentially at equal angles between one another. For example, if there are three lobes 51, the angular spacing would be about 120° between the radial center line of each of the lobes 51. In the case of four lobes, the spacing would be about 90°. As seen in FIG. 1, the end 55 of each of the lobes 51 is curved at least at the corners between the respective end 55 and the walls 59 forming a channel 61. The lobes 51 overlap at a central portion of the pilot hole 33 for receipt of the shank 13 therein. Spandrels 65 are formed in areas between adjacent walls 59 and provide a transition between adjacent lobes 51. The purchase areas 37 are formed in the spandrels 65.

After the pilot hole 33 is formed, as described above with the effector 35, the screw 11 is threaded into the pilot hole with the thread 15 of the shank 13 engaging bone material in the purchase areas 37. Preferably, the entire depth of the thread 15, i.e., the surface defining the root 17 of the thread will be engaged with the bone material. Preferably, there will be interference between the root surface 14 and the bone 21. As best seen in FIG. 5, the angle A of the outer edge of the thread 15 engaging in the bone 21 will be in the range of between about 60° and about 200° of the outer perimeter of the thread 15 at the outer surface of the bone 21 surrounding the shank 13. The angle A measurement is taken at the top surface of the bone at the outer perimeter of the last full turn of the thread 15 engaging the bone 21.

In a preferred embodiment, each of the lobes 51 are sized and shaped to provide an open space between the outer perimeter of the thread 15 and the most radially outward portion of a respective end 55 of each of the lobes 51, a distance S of at least about ⅛ inch. This open area of the pilot hole 33 allows for the insertion of bone inducing growth material, such as demineralized bone, morselized bone, bone cement and the like, to be inserted into the pilot hole 33 to induce bone growth between the bone 21 and the portions of the screw thread 15 that are exposed in the pilot hole 33.

In the practice of the present invention, the surgical site 31 is exposed for the surgical procedure. The pilot hole 33 is formed with the effector 35 by machining each of the lobes 51 to the desired position, size and shape, which will be determined by the screw to be used. The shank 13 is then suitably driven into the pilot hole 33 with the thread 15 engaging the purchase areas 37. The size and shape of the pilot hole 33 will be determined by such factors as the major diameter of the shank 13, the root diameter of the shank 13, and the quality of the bone 21, in addition to other factors as are known in the art. The selected screw 11 is then driven into the pilot hole 33. If the screw 11 is a pedicle screw, then a rod or the like would be subsequently secured to the tulip 19 as is known in the art.

The term "about", as used herein regarding quantitative dimensions and angles, is used to recognize that those measurables cannot be measured with high precision using commonly available measuring devices, and that they are difficult to measure given the types of materials that are being measured; for example, rough and non-uniform. It is also recognized that different people measuring the same thing will often obtain different results, particularly given different measuring environments. These variations, though, are inconsequential to the invention. The term also includes manufacturing limitations that result in inexact cutting and measurements, particularly with respect to materials such as bone that vary from patient to patient.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention and that the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for securing a bone screw to a bone in a surgical procedure comprising:

a surgical screw having a cylindrical shank section, said shank portion having at least one helical thread for engaging bone material, said at least one helical thread having a major thread diameter that is the diameter of an imaginary coaxial cylinder that just touches the crest of said at least one helical thread, said surgical screw having a minor or root diameter which is the diameter of an imaginary cylinder that just touches the root of said at least one helical thread, a pilot hole formed into a bone, said pilot hole having a plurality of lobes, said lobes projecting radially outwardly from a center of said pilot hole, and spaced circumferentially apart with respect to each other, said lobes overlapping at a central portion of said pilot hole so that said pilot hole is sized for receipt of said shank therein, spandrels formed in areas between adjacent walls of said lobes provide a transition between adjacently positioned lobes, said spandrels forming purchase areas for said helical thread, said lobes sized and shaped to provide an open space between said major thread diameter and a most radially outward portion of a respective end of each said lobe, an effector configured to create the pilot hole and the plurality of lobes, the effector coupled to a machining element attached to a shaft coupled to a drive device that is part of a surgical robot that controls operation of the machining element.

2. The system for securing a bone screw to a bone of claim 1 wherein said open space between said major thread diameter and said most radially outward portion of a respective end of each said lobe is sufficient for the insertion of a bone inducing growth material.

3. The system for securing a bone screw to a bone of claim 1 wherein said open space between said major thread diameter and said most radially outward portion of a respective end of each said lobe is sufficient for the insertion of a plurality of bone fragments.

4. The system for securing a bone screw to a bone of claim 1 wherein said open space between said major thread diameter and said most radially outward portion of a respective end of each said lobe is at least one eighth of an inch.

5. The system for securing a bone screw to a bone of claim 1 wherein each of said plurality of lobes are spaced at substantially equal angles with respect to each other.

6. The system for securing a bone screw to a bone of claim 1 wherein said pilot hole includes at least three said lobes.

7. The system for securing a bone screw to a bone of claim 1 wherein said pilot hole includes at least four said lobes.

8. The system for securing a bone screw to a bone of claim 1 wherein said shank portion is tapered at a distal end thereof.

9. The system for securing a bone screw to a bone of claim 8 wherein said surgical screw is self-tapping.

10. The system for securing a bone screw to a bone of claim 1 wherein said shank includes a plurality of lobes, an outer perimeter of each said lobe including segments of said helical thread.

11. The system for securing a bone screw to a bone of claim 10 wherein said shank includes three said lobes.

12. The system for securing a bone screw to a bone of claim 1 wherein said surgical screw is a pedicle screw.

13. The system for securing a bone screw to a bone of claim 1 wherein said surgical screw is a poly-axial pedicle screw.

14. The system for securing a bone screw to a bone of claim 1 wherein said surgical screw is a mono-axial pedicle screw.

15. The system for securing a bone screw to a bone of claim 1 wherein said helical thread includes two different thread pitches along the length of said helical thread.

\* \* \* \* \*